United States Patent
Yoon et al.

(10) Patent No.: US 10,662,887 B2
(45) Date of Patent: May 26, 2020

(54) FUEL MIXING OCCURRENCE DETECTION DEVICE AND FUEL MIXING OCCURRENCE DETECTION METHOD USING FUEL PROPERTY

(71) Applicants: Hyundai Motor Company, Seoul (KR); Kia Motors Corporation, Seoul (KR)

(72) Inventors: Il-O Yoon, Seoul (KR); Min-Jung Bae, Daegu (KR); Choong-Seob Park, Gyeonggi-do (KR)

(73) Assignees: Hyundai Motor Company, Seoul (KR); Kia Motors Company, Seoul (KR)

( * ) Notice: Subject to any disclaimer, the term of this patent is extended or adjusted under 35 U.S.C. 154(b) by 0 days.

(21) Appl. No.: 16/212,895

(22) Filed: Dec. 7, 2018

(65) Prior Publication Data
US 2019/0257262 A1    Aug. 22, 2019

(30) Foreign Application Priority Data
Feb. 21, 2018   (KR) ........................ 10-2018-0020505

(51) Int. Cl.
*F02D 41/30*   (2006.01)
*F02D 41/22*   (2006.01)
(Continued)

(52) U.S. Cl.
CPC ......... *F02D 41/22* (2013.01); *F02D 19/0623* (2013.01); *F02D 41/0025* (2013.01); *G01N 33/2829* (2013.01); *F02C 9/30* (2013.01); *F02D 2041/225* (2013.01); *F02D 2041/228* (2013.01); *F02D 2200/0602* (2013.01); *F02D 2200/0611* (2013.01)

(58) Field of Classification Search
CPC .. F02D 41/3082; F02D 41/22; F02D 19/0623; F02D 2041/225; F02D 2041/228; F02D 2200/0602; F02D 2200/0611; G01N 33/2829
USPC ....... 123/1 A, 446, 457, 491, 497, 498, 499, 123/510, 511, 576, 179.17; 701/103–105, 701/113; 73/114.41, 114.42, 114.43
See application file for complete search history.

(56) References Cited

U.S. PATENT DOCUMENTS 4,577,604 A * 3/1986 Hara ...................... F02M 37/08
                                                        123/358
5,842,454 A * 12/1998 Miwa .................. F02D 41/3082
                                                        123/497
(Continued)

FOREIGN PATENT DOCUMENTS

| KR | 10-0568265 B1 | 3/2006 |
|---|---|---|
| KR | 10-2014-0032603 A | 3/2014 |
| KR | 10-1762406 B1 | 7/2017 |

*Primary Examiner* — Hai H Huynh
*Assistant Examiner* — Gonzalo Laguarda
(74) *Attorney, Agent, or Firm* — Mintz Levin Cohn Ferris Glovsky and Popeo, P.C.; Peter F. Corless (57) ABSTRACT

A fuel mixing occurrence detection device is provided. The device includes a fuel-type identification unit that identifies a type of fuel injected into a vehicle by comparing a fuel pump drive RPM for achieving target fuel pressure with a predetermined reference value upon starting of the vehicle. A communication unit transmits a fuel mixing occurrence to an in-vehicle controller in response to determining that the fuel mixing has occurred.

17 Claims, 5 Drawing Sheets

(51) Int. Cl.
*F02D 19/06* (2006.01)
*G01N 33/28* (2006.01)
*F02D 41/00* (2006.01)
*F02C 9/30* (2006.01)

(56) References Cited

U.S. PATENT DOCUMENTS

| | | | | |
|---|---|---|---|---|
| 6,446,614 B1 * | 9/2002 | Matsuoka | ............... | F02D 29/06 123/516 |
| 2009/0031987 A1 * | 2/2009 | Tanaka | ................ | F02D 41/0025 123/406.3 |

* cited by examiner

FUEL MIXING OCCURRENCE DETECTION DEVICE AND FUEL MIXING OCCURRENCE DETECTION METHOD USING FUEL PROPERTY

CROSS-REFERENCE(S) TO RELATED APPLICATIONS

This application claims priority to Korean Patent Application No. 10-2018-0020505, filed on Feb. 21, 2018, which is incorporated herein by reference in its entirety.

BACKGROUND

Field of the Disclosure

The present disclosure relates to a fuel mixing occurrence detection device and a fuel mixing occurrence detection method, and more particularly, to a device and a method for detecting whether fuel mixing has been injected into a vehicle using the density property of the fuel.

Description of Related Art

Vehicles use different types of fuels, such as gasoline, diesel, and liquefied petroleum gas (LPG). Particularly, since gasoline and diesel are simultaneously treated at a general gas station, there is a risk of a fuel mixing accident in which different types of fuel other than the designated fuel is injected into the vehicle, such as injecting diesel into a gasoline vehicle or injecting gasoline into a diesel vehicle. When the fuel mixing accident occurs, the engine may not start, or even if the engine starts, the output decreases to stop the engine, which causes noise or vibration and further damages the engine. Recently, due to an increase in the fuel mixing accidents, a technology for preventing the fuel mixing accident or detecting the fuel mixing occurrence fact has been developed.

In one related art, by sensing the vehicle noise to select a fuel type suitable for the corresponding vehicle and operating the gas pump based on the above, it is possible to prevent in advance the fuel mixing accident occurring during fuel filling. In another related art, by sensing the fuel type of the vehicle using a camera and operating the gas pump based on the above, it is possible to prevent in advance the fuel mixing accident occurring during fuel filling. In yet another related art, by attaching the electronic identification tag to the vehicle and recognizing the electronic identification tag through the recognition unit installed at the gas station to identify the fuel type suitable for the vehicle, it is possible to prevent in advance the fuel mixing accident occurring during fuel filling.

In the above related art technologies, since a particular type of sensing unit is required to be installed at the gas station to identify the fuel type suitable for the vehicle, the suitable fuel type may not be properly identified without such a sensor. For example, a particular electronic identification tag is also separately required for the vehicle as well as for the gas station.

The contents described in Description of Related Art are to help the understanding of the background of the present disclosure, and may include what is not previously known to those skilled in the art to which the present disclosure pertains.

SUMMARY

When a fuel mixing accident occurs, the fuel in a vehicle should be removed rapidly, and the interior of a fuel tank should be cleaned and dried. However, despite the occurrence of the fuel mixing accident, when the driver does not recognize the fuel mixing fact and operates the vehicle, the above measures are delayed and thus, the engine may require replacement due to the engine failure. In addition, there is a possibility that a major accident may occur due to the KEY-OFF, etc. during driving.

Accordingly, the driver should be promptly informed when the fuel mixing accident occurs to induce the driver to take appropriate measures as described above. However, in the related art technologies, in order to recognize the fuel mixing occurrence, a special sensing unit is required to be installed in the gas station, and it may be difficult for a general driver of a vehicle using a gas station facility having no such special unit to recognize the fuel mixing occurrence.

As described above, other than visually ensuring the correct fuel type, until now, to prevent fuel mixing accident and immediately recognize the fuel mixing accident occurrence, there has been no other way than to rely on a particular unit installed outside the vehicle.

The present disclosure provides a fuel mixing occurrence detection device and a fuel mixing occurrence detection method, which may immediately recognize the fuel mixing occurrence using the components already mounted within the vehicle to warn a driver without relying on a special unit provided outside the vehicle, thus preventing damage caused by the fuel mixing accident. As a result of the repeated research, the inventors of the present disclosure have found that the type of fuel injected may be identified using the measured result of the drive revolutions per minute (RPM) of the fuel pump that has been not mainly monitored upon the starting, conventionally, from the relationship between the fuel density and the fuel pressure.

In particular, the fuel mixing occurrence detection device and the fuel mixing occurrence detection method may compare the drive RPM of the fuel pump for achieving the target fuel pressure with a predetermined reference value to identify the type of fuel injected into the vehicle, thus determining whether the fuel mixing has occurred and warning the driver of such an occurrence.

The fuel mixing occurrence detection device in accordance with the present disclosure may include a fuel-type identification unit configured to identify a type of fuel injected into a vehicle by comparing a fuel pump drive RPM for achieving target fuel pressure with a predetermined reference value upon starting of the vehicle; and a communication unit configured to transmit a fuel mixing occurrence fact to an in-vehicle controller in response to determining that the fuel mixing has occurred as a result of identifying the fuel type in the fuel-type identification unit. The fuel mixing occurrence detection device may further include an engine controller configured to determine whether fuel is injected from information regarding the fuel amount in a fuel tank sensed using a fuel amount sensor installed on the fuel tank.

Additionally, the engine controller may be configured to determine fuel pressure required for the starting of the vehicle from the information regarding the fuel amount in the fuel tank, and input the information regarding the determined fuel pressure value to the fuel-type identification unit. The fuel-type identification unit may be configured to receive the measured result of the RPM of a fuel pump at the time of reaching starting target fuel pressure from a measurement sensor configured to measure the drive RPM of the fuel pump, and determine that fuel mixing accident has occurred in response to determining that the measured RPM of the fuel pump exceeds a predetermined RPM range of the fuel pump corresponding to the fuel type of the corresponding vehicle.

According to an exemplary embodiment of the present disclosure, the vehicle may be a gasoline vehicle, and the fuel-type identification unit may be configured to receive the measured result of the RPM of a fuel pump at the time of reaching starting target fuel pressure from a measurement sensor configured to measure the RPM of the fuel pump, and determine that illegal or incorrect gasoline has been injected in response to determining that the measured RPM of the fuel pump exceeds a predetermined RPM range of the fuel pump corresponding to genuine quality gasoline.

In response to determining that the fuel mixing accident has occurred by the fuel-type identification unit, the communication unit may be configured to provide a notification regarding a fuel mixing occurrence to the engine controller. In response, the engine controller may be configured to turn off an engine. The fuel mixing occurrence detection device may further include a fuel mixing occurrence alarm unit; and as a result of identifying the fuel type in the fuel-type identification unit and determining that the fuel mixing has occurred, the communication unit may be configured to provide a notification of a fuel mixing occurrence to the fuel mixing occurrence alarm unit. In response, the fuel mixing occurrence alarm unit may be configured to operate and flash a warning lamp of the instrument panel of the vehicle to warn a driver of the fuel mixing occurrence.

Further, the fuel mixing occurrence detection device may include a fuel mixing occurrence alarm unit, and as a result of identifying the fuel type in the fuel-type identification unit and determining that illegal gasoline has been injected, the communication unit may be configured to provide a notification regarding the injection of the illegal gasoline to the fuel mixing occurrence alarm unit. In response, the fuel mixing occurrence alarm unit may be configured to operate and flash a warning lamp of the instrument panel of the vehicle to warn the driver regarding the injection of the illegal gasoline.

The fuel controller may be configured to determine that a fuel leakage has occurred when the fuel amount upon the starting of the vehicle decreases by a predetermined range or more compared to the fuel amount finally stored before the starting of the vehicle, and output a warning to the driver regarding the leakage using an alarm unit installed in the vehicle. The measurement sensor configured to measure the drive RPM of the fuel pump may be configured to directly measure the RPM of the motor using an angle sensor or a hall sensor installed on the drive motor of the fuel pump, or measure the drive RPM using a counter electromotive force generated upon the rotation of the drive motor.

A fuel mixing occurrence detection method in accordance with the present disclosure may include receiving target fuel pressure required for the starting upon the starting of an engine from an engine controller; receiving the drive RPM of a fuel pump measured at the time of reaching the target fuel pressure after the starting of the engine from a drive RPM measurement sensor of the fuel pump; determining the fuel-type identification and whether fuel mixing occurs by comparing the measured drive RPM of the fuel pump with the predetermined range of a drive RPM of the fuel pump corresponding to a fuel type of the corresponding vehicle; and outputting a fuel mixing occurrence notification to a controller installed within a vehicle in response to determining that the fuel mixing has occurred.

The fuel mixing occurrence detection method may further include determining whether fuel is injected before the starting of the vehicle, and fuel-type identification for determining whether the fuel mixing has occurred may be started by sensing the change in the fuel amount in the fuel tank before the starting of the vehicle to determine that a new fuel has been injected when the fuel amount increases by a predetermined range or more.

Additionally, the fuel mixing occurrence detection method may include determining whether illegal or incorrect gasoline has been injected in response to determining that the measured drive RPM of the fuel pump is included in the predetermined range of the drive RPM of the fuel pump corresponding to a fuel type of the corresponding vehicle. Additionally, the determining of whether the illegal gasoline has been injected may include determining whether the measured RPM of the fuel pump has exceeded the predetermined range of the RPM of the fuel pump corresponding to the genuine quality of gasoline.

The controller may be the engine controller, and in response to determining that the fuel mixing has occurred, the engine controller may be configured to turn off the starting of the vehicle. Particularly, the controller may be configured to operate an alarm unit mounted within the vehicle, and in response to determining that the fuel mixing has occurred, a warning may be output to the driver regarding the fuel mixing occurrence using the alarm unit. In response to determining that the illegal gasoline has been injected, a notification regarding the injection of the illegal gasoline may be provided to a driver using the alarm unit.

Further, the fuel mixing occurrence detection method may include determining whether a fuel leakage, when the fuel amount upon the starting of the vehicle decreases by a predetermined range or more compared to the fuel amount finally stored before the starting of the vehicle. In response to determining that the fuel leakage has occurred, a notification regarding the fuel leakage may be provided to a driver using an alarm unit mounted within the vehicle.

According to the present disclosure, when the fuel mixing accident occurs, the driver may be warned rapidly regarding the fuel mixing occurrence thus preventing a failure of the engine system due to the vehicle driving in the fuel mixing state and the increase in the repair cost due to the failure. In addition, it may be possible to prevent a situation in which the driver operates the vehicle without recognizing the fuel mixing occurrence, thus preventing the potential of a second accident due to the malfunction during vehicle driving.

The fuel mixing detection method and the fuel mixing detection device in accordance with the present disclosure may utilize the components already mounted within the vehicle by changing software without installing any additional components in the vehicle for detecting the fuel mixing occurrence, thus alleviating the driver anxiety regarding the fuel mixing accident occurrence without a separate additional cost.

BRIEF DESCRIPTION OF THE DRAWINGS

A brief description of each drawing is provided to more sufficiently understand drawings used in the detailed description of the present invention.

DETAILED DESCRIPTION

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

Furthermore, control logic of the present invention may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Hereinafter, the present disclosure will be described in detail with reference to the accompanying drawings.

Figure 1:
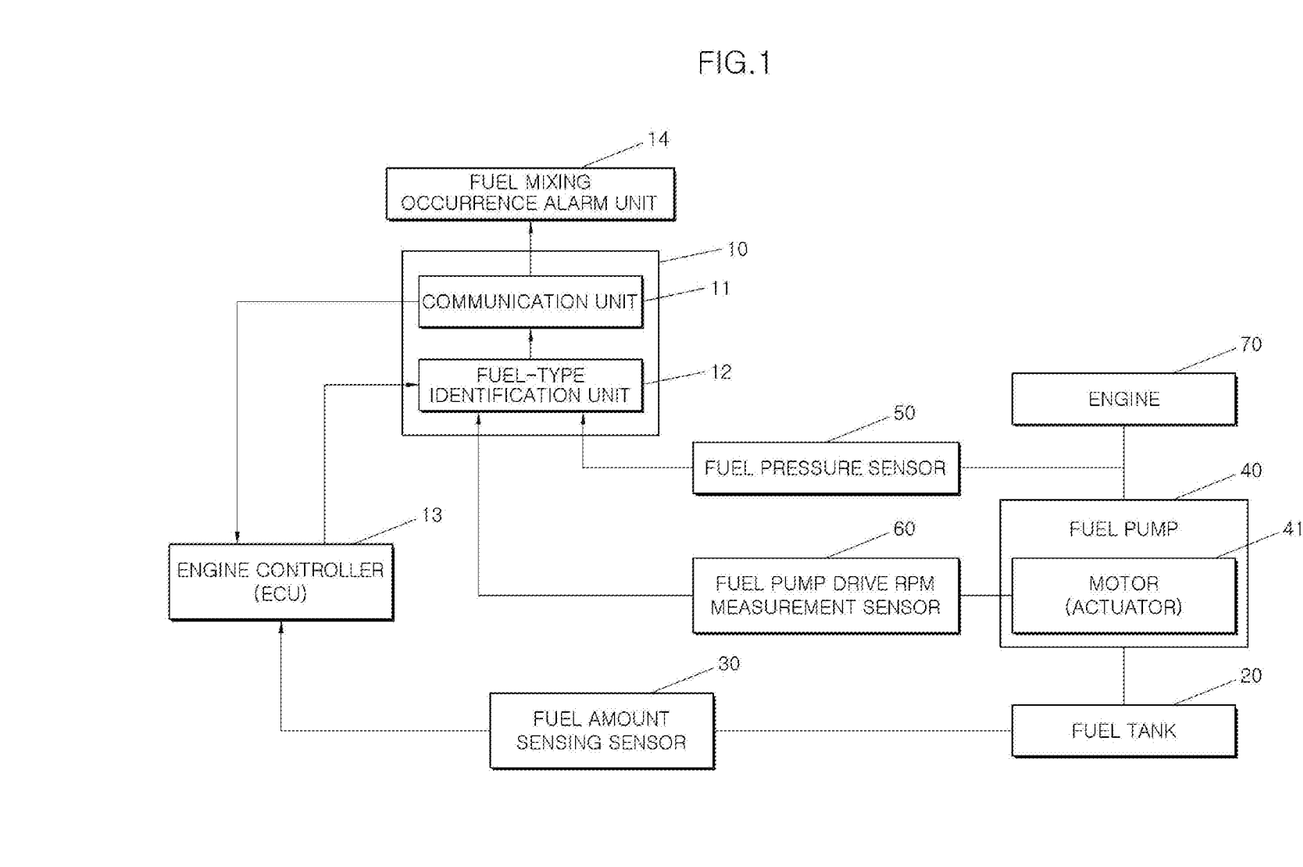
FIG. 1 is a block diagram illustrating a configuration of a fuel mixing detection device in accordance with an exemplary embodiment of the present disclosure.

FIG. 1 is a block diagram illustrating a configuration of a fuel mixing detection device in accordance with an exemplary embodiment of the present disclosure. As illustrated in FIG. 1, the fuel mixing detection device in accordance with the exemplary embodiment of the present disclosure may include a fuel-type identification unit 12 configured to identify the type of fuel injected into a vehicle by comparing a drive RPM of a fuel pump 40 for achieving target fuel pressure with a predetermined reference value upon the start of the vehicle, and a communication unit 11 configured to transmit a fuel mixing occurrence notification to an in-vehicle controller in response to determining that the fuel mixing occurs as a result of identifying the fuel type in the fuel-type identification unit 12. The fuel-type identification unit 12 and the communication unit 11 may be components of a fuel pump control module 10 installed in advance for operating the fuel pump 40.

The fuel pump control module 10 may be configured to receive information regarding the present fuel pressure from a fuel pressure sensor 50, configured to measure the fuel pressure of the fuel supplied from the fuel pump 40 to an engine 70 through a supply line, via controller area network (CAN) communication, etc. In response receiving the starting target fuel pressure from an engine controller 13, the fuel pump control module 10 may be configured to determine a control duty value of a motor 41 of the fuel pump 40 for controlling feedback to adjust the present fuel pressure to correspond to the starting target fuel pressure, and operate the motor 41 based on the determined control duty value. Accordingly, the fuel pump control module 10 feedback-controls the motor 41 to cause the current fuel pressure to reach the starting target fuel pressure while measuring the current fuel pressure using the fuel pressure sensor 50.

A fuel pump drive revolutions per minute (RPM) measurement sensor 60 may be configured to measure the RPM of the motor 41 of the fuel pump 40, and transmit information regarding the measured RPM to a fuel-type identification unit 12 via CAN communication, etc. When the motor includes an angle sensor configured to calculate the angle of the motor to determine the amount of rotation or a hall sensor configured to directly count the RPM, etc., the fuel pump drive RPM measurement sensor 60 may be configured to measure the RPM using the sensor. When the sensor is not provided in the motor, the fuel pump drive RPM measurement sensor 60 may be configured to count the counter electromotive force generated upon the rotation of the motor, and measure the RPM of the motor using a method of estimating the RPM of the motor.

A vehicle having the fuel mixing detection device in accordance with the present disclosure may include a fuel tank 20 in which a specified fuel is stored and a fuel amount sensing sensor 30 installed within the fuel tank. The fuel amount sensing sensor 30 may be configured to measure the displacement of a float floating on the fuel in the fuel tank 20 (e.g., the change in height of the float based on the volume of fuel within the tank) to measure the level of the remaining fuel amount to determine the remaining fuel amount. The information regarding the remaining fuel amount measured by the fuel amount sensing sensor 30 may be transmitted to the engine controller 13 of the vehicle via CAN communication, etc.

The engine controller 13 may be configured to calculate the fuel pressure necessary for starting from the remaining fuel amount information of the fuel tank 20 measured using the fuel amount sensing sensor 30, and transmit the fuel pressure calculated for the fuel-type identification to the fuel-type identification unit 12. In addition, as will be described later, in response to receiving the fuel mixing occurrence fact from the communication unit 11 via CAN communication, etc., the engine controller 13 may be configured to turn off the engine to prevent damage to engine components due to the fuel mixing. In addition, the engine controller 13 may be configured to, as will be described later, determine whether a new fuel is injected and whether the fuel has leaked by determining whether the fuel amount sensed by the fuel amount sensing sensor is increased or decreased. Since the fuel-type identification is required when the new fuel is injected, when it is possible to determine whether the new fuel is injected, whether a fuel-type identification mode, which will be described later, will be started may be determined.

As illustrated in FIG. 1, the fuel stored in the fuel tank 20 may be pumped by the fuel pump 40 and supplied to the engine 70 through the supply line. More specifically, the fuel pumped by the fuel pump 40 may be compressed by a greater pressure through a high-pressure system including a high-pressure pump which is not illustrated and supplied to an injector of the engine 70, and the fuel supplied to the injector injects the compressed fuel into the cylinder of the engine 70 to supply the fuel to the engine 70. Generally, when the engine start request is made by the driver, the engine controller 13 may be configured to calculate the fuel pressure required for starting from the remaining fuel amount information of the fuel tank 20 measured using the fuel amount sensing sensor 30, and determine whether the measured fuel pressure from the fuel pressure sensor 50 satisfies the calculated fuel pressure. In response to determining that the measured fuel pressure satisfies the calculated fuel pressure, the fuel may be supplied into the cylinder of the engine 70 to start the engine.

As described above, in the conventional case, the fuel pump control module 10 has been monitoring only the current fuel pressure to determine whether the fuel pressure has reached the starting target fuel pressure of the engine 70. Accordingly, the RPM of the motor 41 of the fuel pump 40 at the corresponding timing has been not monitored. However, the magnitude of the fuel pressure is determined by the sum of the positive pressure and the dynamic pressure, and in this time, the dynamic pressure of the fuel is determined by the following Equation 1.

$$Pd = \frac{1}{2} \times p \times v^2 \qquad \text{Equation 1}$$

wherein, the Pd refers to the dynamic pressure of the fuel, the $\rho$ to the density of the fuel, and the v to the flow rate of the fuel.

However, when the types of the fuel are different, the densities thereof also become different. For example, at a temperature of 15° C., the density of gasoline is 0.702 kg/l and the density of diesel is 0.876 kg/l, with a difference of about 20%. According to the Equation 1, when the densities are different, the flow rate should be increased to produce the same pressure. In other words, when the fuel types are different, the flow rate of the fuel for reaching the starting target fuel pressure is changed, and thereby, the RPM of the motor 41 of the fuel pump 40 at the time of reaching the starting target fuel pressure is also changed.

For example, assuming that the fuel pressure required for starting is 6 bar, a flow rate of 3.7 m/s is required for diesel and a flow rate of 4.2 m/s for gasoline, and both have the difference of the flow rate of about 10% under the same fuel pressure. Accordingly, the RPM of the motor 41 of the fuel pump 40 required for satisfying the fuel pressure of 6 bar becomes also different for both.

Figure 3:
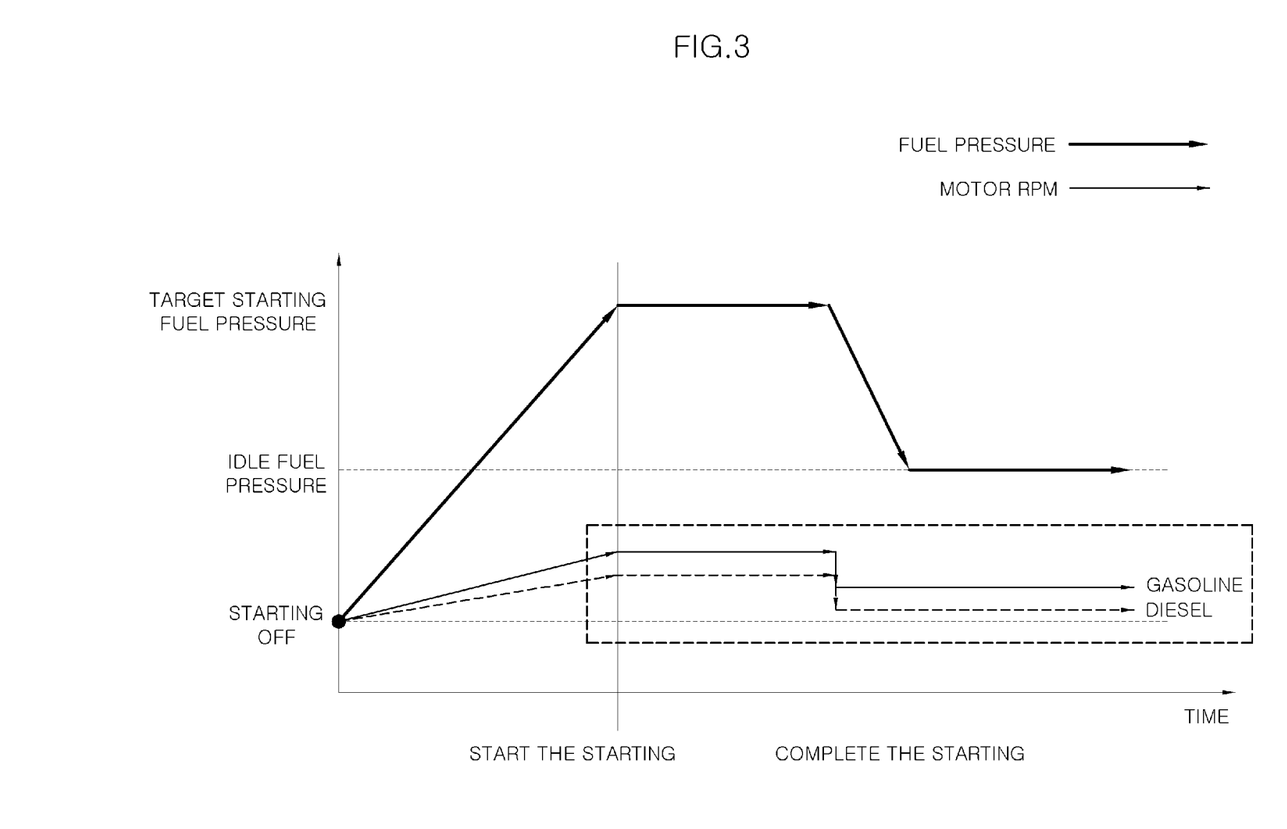
FIG. 3 is a graph for explaining the fuel mixing detection principle of gasoline and diesel in accordance with an exemplary embodiment of the present disclosure.

This is well illustrated in FIG. 3. When the operation of the motor 41 of the fuel pump 40 is started based on the control duty of the fuel pump control module 10, the fuel pressure and the RPM of the motor 41 increase. Through the measurement result of the fuel pressure sensor 50, the fuel pump control module 10 performs feedback control increasing the RPM of the motor 41 until it is determined that the starting target fuel pressure has been reached. Then, in response to determining that the target fuel pressure has been reached, the engine controller 13 starts the starting.

As described above, due to the difference in density between the gasoline and the diesel, the RPM of the motor 41 becomes different at the timing of reaching the target fuel pressure. Whether the fuel newly injected is suitable for the corresponding vehicle may be determined when measuring the RPM of the motor 41 at the time of reaching the target fuel pressure to compare it with a predetermined reference value.

According to the aspect of the present disclosure, when the RPM of the motor 41 exceeds the allowable range of the predetermined reference value at the time of reaching the target fuel pressure, a different type of the fuel injection may be determined. For example, when diesel is injected into the gasoline vehicle, the RPM of the motor 41 at the time of reaching the target fuel pressure is beyond the allowable range of the RPM of the motor 41, which is generally allowed when the gasoline is injected, and thus a fuel mixing occurrence may be detected.

Accordingly, the fuel-type identification unit 12 in accordance with the exemplary embodiment of the present disclosure may be configured to compare the drive RPM of the fuel pump 40 for achieving the target fuel pressure with a predetermined reference value upon the start of the vehicle to determine that the fuel mixing accident has occurred when it beyond the allowable range of the reference value. As a result of identifying the fuel type in the fuel-type identification unit 12, in response to determining that the fuel mixing has occurred, the communication unit 11 may be configured to transmit a notification regarding the fuel mixing occurrence to the in-vehicle controller.

The communication unit 11 may then be configured to transmit the fuel mixing occurrence notification to a fuel mixing occurrence alarm unit 14. In response to receiving the notification, the fuel mixing occurrence alarm unit 14 may be operated to flash a warning lamp installed on the instrument panel of the vehicle to warn a driver of the fuel mixing occurrence. As a result, the driver may rapidly respond by, for example, removing fuel from the vehicle, and cleaning and drying the inside of the fuel tank, thus preventing additional component damage to the vehicle.

In addition, the communication unit 11 may be configured to transmit a notification regarding the fuel mixing occurrence to the engine controller 13 via CAN communication, etc. In response to receiving the notification, the engine controller 13 may be configured to turn off the engine 70 to prevent the fuel mixing component from being injected into the engine 70. As a result, it may be possible to prevent damage to the engine 70 due to the fuel mixing.

Figure 4:
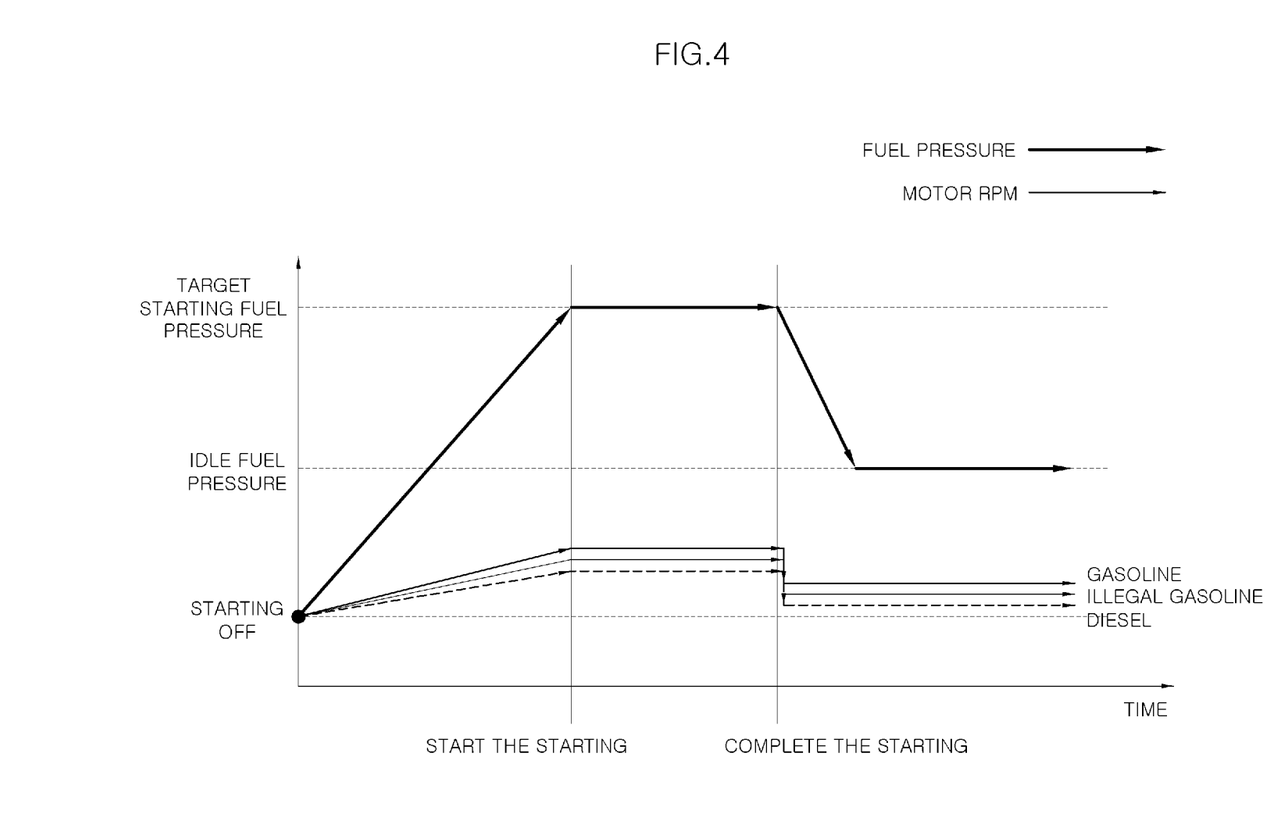
FIG. 4 is a graph for explaining the illegal gasoline detection principle in accordance with an exemplary embodiment of the present disclosure.

Using the principle of the present disclosure, two completely different fuels may be mixed, and also, as illustrated in FIG. 4, in a gasoline vehicle, it may be possible to determine whether bad fuel such as illegal or incorrect gasoline is injected into the fuel tank. Since illegal gasoline has a slightly different composition compared to genuine gasoline, the density thereof is also different from genuine gasoline. Accordingly, even when the illegal gasoline is injected, the drive RPM of the fuel pump 40 for achieving the target fuel pressure is different from that of when the genuine gasoline is injected. As illustrated in FIG. 4, the difference is relatively small as compared with the cases of diesel and gasoline, however, by more accurately adjusting the numerical range of the RPM of the motor which may be recognized as genuine gasoline, whether the illegal gasoline is injected may be determined using the same principle.

As a result of identifying the fuel-type identification unit 12, in response to determining that the illegal gasoline is injected, the communication unit 11 may be configured to transmit a notification regarding the illegal gasoline injection to the fuel mixing occurrence alarm unit 14. In response, the fuel mixing occurrence alarm unit 14 may be configured to flash a warning lamp installed on the instrument panel of the vehicle to warn to the driver of the illegal gasoline injection. As a result, it may be possible to induce the driver to respond accordingly.

Figure 2A:
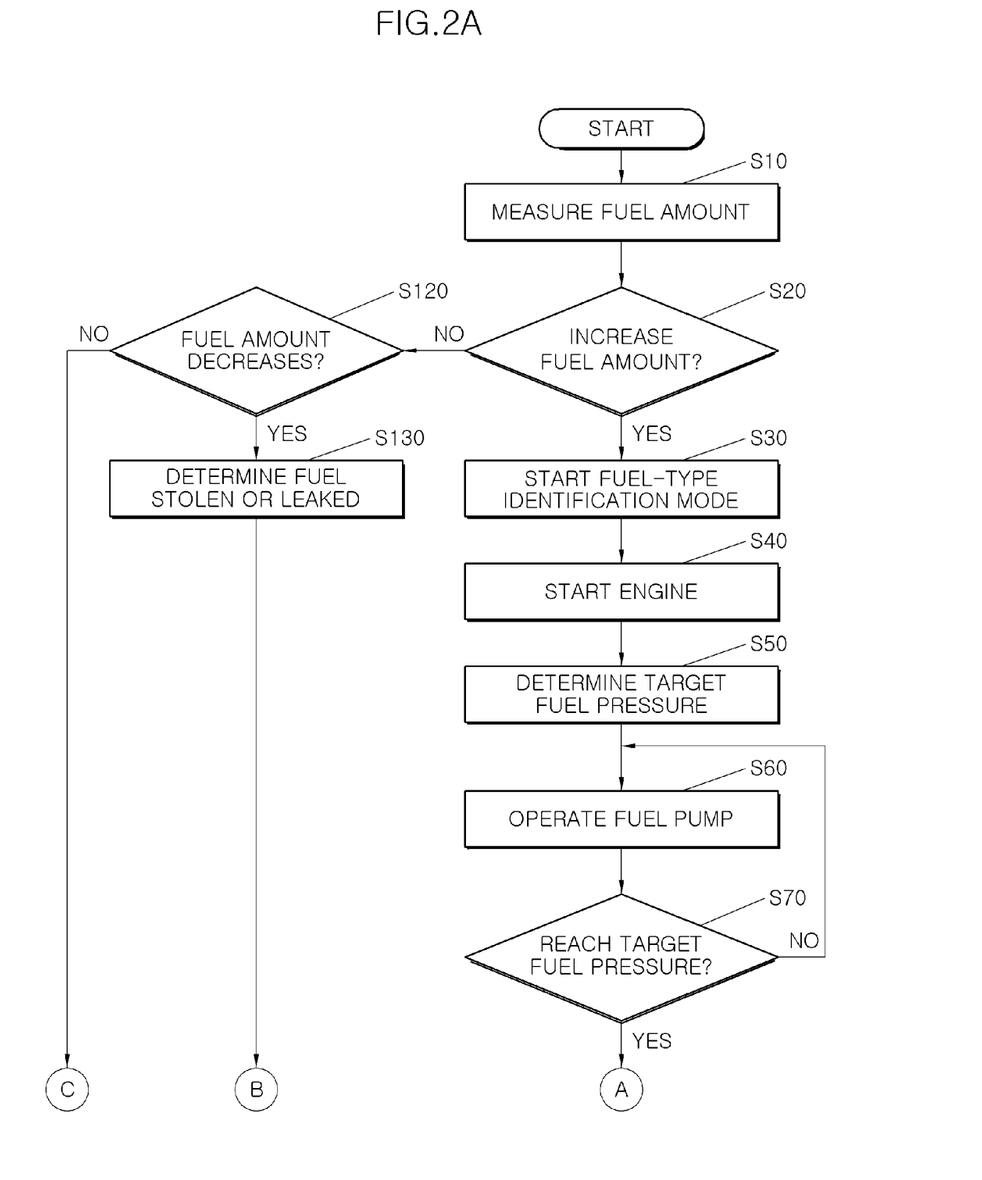
FIG. 2A and FIG. 2B are flowcharts illustrating a fuel mixing detection method in accordance with an exemplary embodiment of the present disclosure.
Figure 2B:
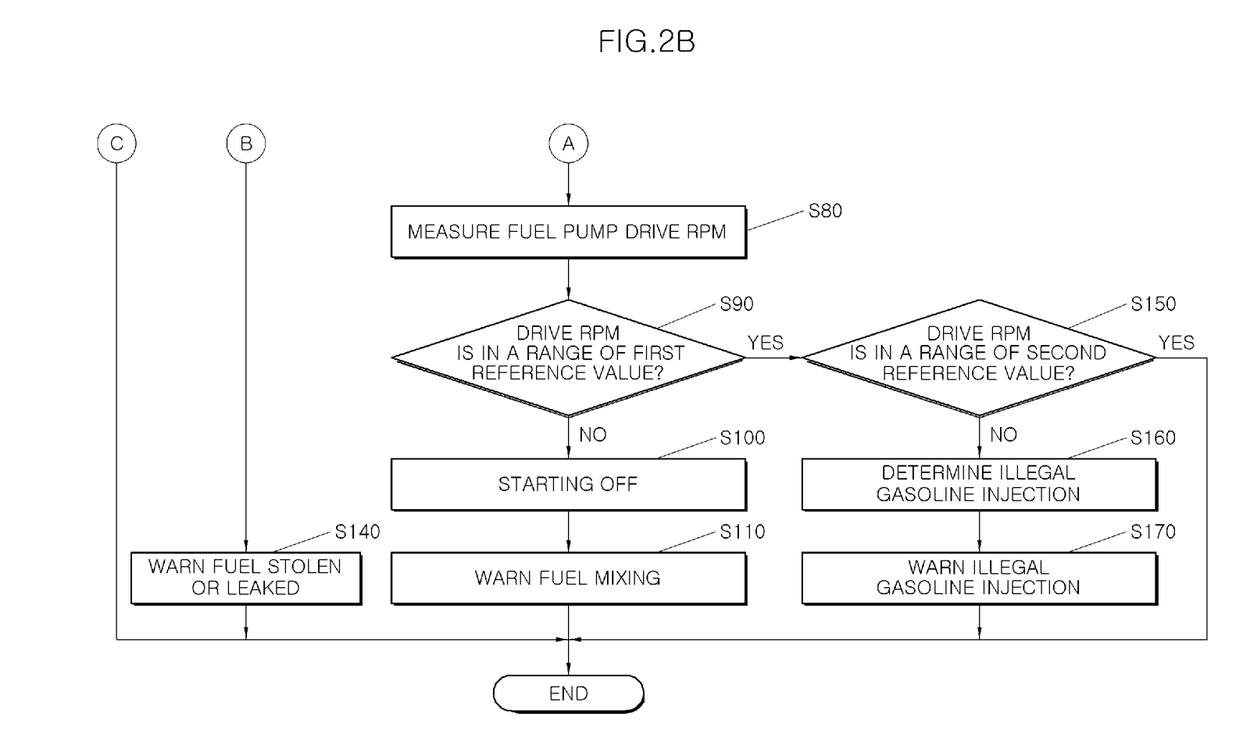

FIGS. 2A and 2B are flowcharts illustrating a fuel mixing detection method in accordance with an exemplary embodiment of the present disclosure. First, the engine controller 13 may be configured to measure the amount of fuel present in the fuel tank 20 using the fuel amount sensing sensor 30 S10. Then, the engine controller 13 may be configured to determine whether the fuel amount is increased by comparing the measured fuel amount of the fuel stored in the fuel tank 20 upon the KEY-OFF just before the starting of the vehicle with the fuel amount of the currently measured fuel S20.

When the current fuel amount of the fuel is greater than the fuel amount of the fuel stored in the fuel tank 20 upon the KEY-OFF just before the starting of the vehicle, the engine controller 13 may be configured to determine that a new fuel has been injected to start a fuel-type identification mode of the newly injected fuel S30. Meanwhile, in response to determining that the current fuel amount of the fuel does not increase compared to the fuel amount of the fuel stored in the fuel tank 20 upon the KEY-OFF just before the starting of the vehicle, the engine controller 13 may be configured to determine that the current fuel amount of the fuel has decreased compared to the fuel amount of the fuel stored in the fuel tank 20 upon the KEY-OFF just before the starting of the vehicle by a predetermined rate or more S120.

In response to determining that the fuel has been decreased by the predetermined rate or more, the engine controller 13 may be configured to determine that the fuel is decreased due to fuel leakage, instead of natural vaporization S130. In particular, the engine controller 13 may be configured to provide a warning or notification regarding the fuel leakage to the driver by flashing a warning lamp on the instrument panel, for example, using the alarm unit installed in the vehicle S140. Additionally, in response to determining that the currently measured fuel amount has no significant increase or decrease compared with the previous one, the control may be terminated since the fuel-type identification is no longer required. After the fuel-type identification mode is started S30, when the engine start request is generated by the driver S40, the engine controller 13 may be configured to calculate the target fuel pressure required for the starting from the amount of fuel remaining in the fuel tank 20 measured using the fuel amount sensing sensor 30 S50.

The information regarding the calculated target fuel pressure may be delivered to the fuel pump control module 10, and the fuel pump control module 10 may be configured to determine the control duty value of the motor 41 of the fuel pump 40 to adjust the current fuel pressure to correspond to the starting target fuel pressure, and operate the motor 41 based on the determined control duty value to operate the fuel pump 40. Accordingly, the fuel pump control module 10 may be configured to continuously determine whether the current fuel pressure has reached the target fuel pressure using the fuel pressure sensor 50 S70, and in addition, feedback-controls the motor 41 to adjust the current fuel pressure to reach the starting target fuel pressure.

In response to determining from the measurement result of the fuel pressure sensor 50 that the current fuel pressure has reached the target fuel pressure, the fuel pump control module 10 may be configured to measure the RPM of the motor 41 operating the fuel pump 40 at that time using the fuel pump drive RPM measurement sensor 60. The fuel-type identification unit 12 may be configured to compare the drive RPM of the fuel pump 40 with a predetermined reference value for the fuel suitable for the vehicle to determine that the fuel mixing accident has occurred when of the drive RPM is beyond the allowable range of the reference value (the range of a first reference value) S90. In response to determining that the fuel mixing accident has occurred, the communication unit 11 may be configured to transmit the fuel mixing occurrence to the in-vehicle controller via CAN communication, etc. In particular, the communication unit 11 may be configured to transmit a notification regarding the fuel mixing occurrence to the engine controller 13 via CAN communication or the like.

In response to receiving the notification regarding the fuel mixing occurrence, the engine controller 13 may prevent the fuel mixing component from being injected into the engine 70 S100. As a result, damage to the engine 70 due to the fuel mixing may be prevented. In addition, the communication unit 11 may be configured to transmit a notification regarding the fuel mixing occurrence to the fuel mixing occurrence alarm unit 14. In response, the fuel mixing occurrence alarm unit 14 may be configured to flash a warning lamp on the instrument panel of the vehicle to provide a warning of the fuel mixing occurrence to the driver S110. As a result, a driver aware of the fuel mixing occurrence may rapidly respond to such an occurrence by, for example, removing fuel from the vehicle, and cleaning and drying the inside of the fuel tank, thereby preventing additional parts damage to the vehicle.

Moreover, the fuel-type identification unit 12 may be configured to compare the drive RPM of the fuel pump 40 at the time of reaching the target fuel pressure with a predetermined reference value for the fuel suitable for the vehicle, and when in the drive RPM is within the allowable range of the reference value (the range of the first reference value), the fuel-type identification unit 12 may be configured to compare the drive RPM of the fuel pump 40 with a predetermined reference value for identifying the illegal gasoline before terminating the control to determine whether in the drive RPM is within the allowable range of the reference value (the range of a second reference value) S150.

In response to determining that the measured RPM of the fuel pump 40 is within the range of the second reference value, the fuel-type identification unit 12 may be configured to determine that the genuine gasoline has been injected and terminate the control. However, in response to determining that the measured RPM of the fuel pump 40 is beyond the range of the second reference value, the fuel-type identification unit 12 may be configured to determine that the illegal gasoline has been injected S160. In response to determining by the fuel-type identification unit 12 that the illegal gasoline has been injected, the communication unit 11 may be configured to transmit a notification regarding the illegal gasoline injection to the fuel mixing occurrence alarm unit 14. The fuel mixing occurrence alarm unit 14 may then be configured to flash a warning lamp on the instrument panel of the vehicle to warn a driver regarding the illegal gasoline injection S170.

According to the measurement method and the measurement unit in accordance with the present disclosure, it may be possible to identify the type of the fuel injected using the existing units (e.g., the fuel pump control module, the engine controller, etc.) already provided in the vehicle, and to detect the fuel mixing occurrence based on the above. In addition, in accordance with the present disclosure, it may be possible to detect fuel mixing of heterogeneous fuel and also the fact that non-genuine illegal gasoline has been injected, thus reliably relieving the driver anxiety about the occurrence of the fuel mixing accident and the injection of low-quality bad gasoline.

What is claimed is:

1. A fuel mixing occurrence detection device, comprising:
   a fuel-type identification unit configured to calculate a target fuel pressure required for starting of a vehicle from a fuel amount in a fuel tank, and once the target fuel pressure is reached, measure a drive revolutions per minute (RPM) of a fuel pump using a measurement sensor, compare the drive RPM of the fuel pump with a predetermined reference value, and determine that a fuel mixing occurrence has occurred when the measured RPM of the fuel pump exceeds the predetermined reference value of the drive RPM of the fuel pump corresponding to a fuel type of the vehicle; and
   a communication unit configured to transmit a notification regarding the fuel mixing occurrence to an in-vehicle controller in response to determining that the fuel mixing has occurred as a result of identifying the fuel type.

2. The fuel mixing occurrence detection device of claim 1, further comprising:
   an engine controller configured to determine whether fuel is injected from information regarding the fuel amount in the fuel tank sensed using a fuel amount sensing sensor installed on the fuel tank.

3. The fuel mixing occurrence detection device of claim 2, wherein the engine controller is configured to determine the target fuel pressure required for the starting of the vehicle from information on the fuel amount in the fuel tank, and input the information regarding the determined target fuel pressure value to the fuel-type identification unit.

4. The fuel mixing occurrence detection device of claim 1, wherein the vehicle is a gasoline vehicle, and wherein the fuel-type identification unit is configured to receive the RPM of the fuel pump at a time of reaching the target fuel pressure from the measurement sensor configured to measure the RPM of the fuel pump, and determine that incorrect gasoline has been injected in response to determining that the measured RPM of the fuel pump exceeds a predetermined RPM range of the fuel pump corresponding to genuine quality gasoline.

5. The fuel mixing occurrence detection device of claim 2, wherein in response to determining that the fuel mixing occurrence has occurred by the fuel-type identification unit, the communication unit is configured to transmit the notification regarding the fuel mixing occurrence to the engine controller, and in response, the engine controller is configured to turn off the engine.

6. The fuel mixing occurrence detection device of claim 2, further comprising:
   a fuel mixing occurrence alarm unit and in response to determining that the fuel mixing has occurred, the communication unit is configured to transmit the notification regarding the fuel mixing occurrence to the fuel mixing occurrence alarm unit,
   wherein the fuel mixing occurrence alarm unit is configured to flash a warning lamp of an instrument panel of the vehicle to warn a driver regarding the fuel mixing occurrence.

7. The fuel mixing occurrence detection device of claim 4, further comprising:
   a fuel mixing occurrence alarm unit and in response to determining that incorrect gasoline has been injected, the communication unit is configured a notification regarding the incorrect gasoline injection to the fuel mixing occurrence alarm unit,
   wherein the fuel mixing occurrence alarm unit is configured to flash a warning lamp of the instrument panel of the vehicle to warn a driver regarding the incorrect gasoline injection.

8. The fuel mixing occurrence detection device of claim 2, wherein the fuel controller is configured to detect a fuel leakage when the fuel amount upon the starting of the vehicle decreases by a predetermined range or more compared to a fuel amount finally stored before the starting of the vehicle, and is configured to provide a warning to a driver regarding the fuel leakage using an alarm unit installed within the vehicle.

9. The fuel mixing occurrence detection device of claim 1, wherein the measurement sensor configured to measure the drive RPM of the fuel pump is configured to directly measure the RPM of the motor using an angle sensor or a hall sensor installed on the drive motor of the fuel pump, or measure the drive RPM using a counter electromotive force generated upon rotation of the drive motor.

10. A fuel mixing occurrence detection method, comprising:
    receiving a target fuel pressure required for starting of a vehicle from a fuel amount in a fuel tank from an engine controller;
    receiving the drive revolutions per minute (RPM) of a fuel pump measured at the time of reaching the target fuel pressure after the starting of the vehicle from a drive RPM measurement sensor of the fuel pump;
    comparing the drive RPM of the fuel pump with a predetermined reference value;
    determining that fuel mixing occurs when the measured drive RPM of the fuel pump exceeds the predetermined reference value of the drive RPM of the fuel pump corresponding to a fuel type of the vehicle; and
    outputting a fuel mixing occurrence notification to a controller installed within the vehicle in response to determining that the fuel mixing has occurred.

11. The fuel mixing occurrence detection method of claim 10, further comprising:
    determining whether fuel is injected before the starting of the vehicle,
    wherein fuel-type identification for determining whether the fuel mixing has occurred is started by sensing a change in the fuel amount in the fuel tank before the starting of the vehicle to determine that a new fuel has been injected when the fuel amount increases by a predetermined range or more.

12. The fuel mixing occurrence detection method of claim 10, further comprising:
    determining whether incorrect gasoline has been injected in response to determining that the measured drive RPM of the fuel pump is included in the predetermined range of the drive RPM of the fuel pump corresponding to a fuel type of the corresponding vehicle; and
    determining whether the measured RPM of the fuel pump has exceeded the predetermined range of the RPM of the fuel pump corresponding to genuine quality gasoline.

13. The fuel mixing occurrence detection method of claim 10, wherein the controller is the engine controller, and wherein in response to determining that the fuel mixing has occurred, the starting becomes OFF by the engine controller.

14. The fuel mixing occurrence detection method of claim 10, wherein the controller is an alarm unit installed in the vehicle, and wherein in response to determining that the fuel mixing has occurred, a warning is provided to a driver using the alarm unit.

15. The fuel mixing occurrence detection method of claim 12, wherein the controller is an alarm unit installed in the vehicle, and wherein in response to determining that the incorrect gasoline has been injected, a warning is provided to a driver regarding the incorrect gasoline injection using the alarm unit.

16. The fuel mixing occurrence detection method of claim 10, further comprising:
   determining whether a fuel leakage has occurred, and
   detecting the fuel leakage when the fuel amount upon the starting of the vehicle decreases by a predetermined range or more compared to the fuel amount finally stored before the starting of the vehicle.

17. The fuel mixing occurrence detection method of claim 16, wherein in response to detecting the fuel leakage, a warning is provided to a driver regarding the fuel leakage using an alarm unit installed within the vehicle.

* * * * *